(12) United States Patent
Miyoshi et al.

(10) Patent No.: US 10,683,485 B2
(45) Date of Patent: Jun. 16, 2020

(54) METHOD FOR CULTURING PRIMARY CELLS

(71) Applicant: Osaka Prefectural Hospital Organization, Osaka-shi, Osaka (JP)

(72) Inventors: Norikatsu Miyoshi, Osaka (JP); Shiki Fujino, Osaka (JP); Masayuki Ohue, Osaka (JP); Masayoshi Yasui, Osaka (JP)

(73) Assignee: OSAKA PREFECTURAL HOSPITAL ORGANIZATION, Osaka-Shi (JP)

( * ) Notice: Subject to any disclaimer, the term of this patent is extended or adjusted under 35 U.S.C. 154(b) by 68 days.

(21) Appl. No.: 15/444,588

(22) Filed: Feb. 28, 2017

(65) Prior Publication Data

US 2018/0023055 A1    Jan. 25, 2018

(30) Foreign Application Priority Data

Jul. 22, 2016    (JP) .................... 2016-144706

(51) Int. Cl.
*C12N 5/09*    (2010.01)
*G01N 33/50*    (2006.01)
*C12N 5/071*    (2010.01)

(52) U.S. Cl.
CPC ......... *C12N 5/0693* (2013.01); *C12N 5/0679* (2013.01); *G01N 33/5005* (2013.01); *G01N 33/5011* (2013.01); *C12N 2503/00* (2013.01); *C12N 2503/02* (2013.01); *C12N 2509/10* (2013.01)

(58) Field of Classification Search
None
See application file for complete search history.

(56) References Cited

U.S. PATENT DOCUMENTS

| | | |
|---|---|---|
| 8,841,125 B2 | 9/2014 | Inoue et al. |
| 2013/0288248 A1 | 10/2013 | Yamazaki et al. |

FOREIGN PATENT DOCUMENTS

| | | |
|---|---|---|
| EP | 2626414 A1 | 8/2013 |
| JP | 2010-227088 A | 10/2010 |
| JP | 2011-115106 A | 6/2011 |
| JP | 2015-062400 A | 4/2015 |
| WO | 2012046797 A1 | 4/2012 |
| WO | 2016/047801 A1 | 3/2016 |

OTHER PUBLICATIONS

Maria Joao Valente et al., A Rapid and Simple Procedure for the Establishment of Human Normal and Cancer Renal Primary Cell Cultures from Surgical Specimens, PLOS ONE, vol. 6, No. 5, May 4, 2011, p. e19337, XP055416048, DOI: 10.1371/journal.pone.0019337 (Relevance is indicated in the EESR dated Oct. 25, 2017 in the corresponding European patent application No. 17182532.6).
Dotse Eunice et al., Isolation of colorectal cancer stem-like cells, Cytotechnology, Kluwer Academic Publishers, Dordrecht, NL, vol. 68, No. 4, Dec. 23, 2014, pp. 609-619, XP036014153, ISSN: 0920-9069, DOI: 10.1007/S10616-014-9806-0 retrieved on Dec. 23, 2014 (Relevance is indicated in the EESR dated Oct. 25, 2017 in the corresponding European patent application No. 17182532.6).
An extended European search report (EESR) dated Oct. 25, 2017 in the corresponding European patent application No. 17182532.6.
He et al., "Isolation and Characterization of Cancer Stem Cells from High-Grade Serous Ovarian Carcinomas", Cell Physiol Biochem., 2014, pp. 173-184, vol. 33, Cellular Physiology & Biochemistry; Relevance is indicated in the Japanese Office Action dated Mar. 10, 2020.
Japanese Office Action dated Mar. 10, 2020 in a counterpart Japanese patent application.

*Primary Examiner* — Blaine Lankford
(74) *Attorney, Agent, or Firm* — Metrolex IP Law Group, PLLC

(57) ABSTRACT

Method for producing a primary culture of cancer cells, comprising: (a) fragmenting cancer tissues derived from a living body and removing impurities from the fragmented cancer tissues, (b) subjecting the tissue masses obtained in (a) to suspension culture, and (c) subjecting the culture obtained in (b) to adherent culture.

2 Claims, 2 Drawing Sheets

| STOMACH CANCER | PANCREATIC CANCER |
|---|---|
| LIVER CANCER | |

| LUNG CANCER | RENAL CANCER |
|---|---|
| BREAST CANCER | |

METHOD FOR CULTURING PRIMARY CELLS

BACKGROUND OF THE INVENTION

The present invention relates to a method for culturing primary cells. More specifically, the present invention relates to a method for producing a primary culture of cancer cells and a method for screening pharmaceuticals and the like using the primary culture of cancer cells obtained by said method.

DESCRIPTION OF THE RELATED ART

It is difficult to completely cure cancers. Especially, gastrointestinal cancers have a high degree of malignancy and complete cure of such cancers is extremely difficult. Established cancer cell lines are commonly used for basic studies on chemotherapies such as anticancer drugs and the like, however the established cancer cell lines have different characteristics from cancer cells under a clinical condition in many aspects, such as morphology and gene expression. For this reason, a primary culture, derived from cancer tissues and thus having characteristics similar to cancer cells under a clinical condition, is preferably used for screenings of anticancer drugs, basic studies on cancer chemotherapies, and the like.

A method for performing primary culture of cells derived from cancer tissues is reported in JP 2010-227088 A. Although this method enables to produce primary cells having characteristics similar to cancer cells under a clinical condition, it is difficult to stably obtain a large amount of primary cells in a simple manner within a short time.

Further, WO 2012/046797 reports a production method of cancer stem cell populations capable of reproducing hierarchical organization of cancer tissues, the method including a step of performing adherent culture after suspension culture. However this method is developed for a different goal from the present invention and requires a step of producing cell masses by transplanting cancer cells to animals.

An object of the present invention is to provide a cancer cell population capable of maintaining characteristics of cancer cells derived from a patient. More specifically, an object of the present invention is to provide a method for performing primary culture in which a large amount of cancer cells derived from a patient can be stably cultured in vitro in a simple manner within a short time. The cancer cell population can be used for elucidating a molecular mechanism of cancer, performing a drug-susceptibility test, and the like in an in vitro culturing system or in a non-human animal model system in which the cancer cell population is transplanted into an animal.

The present inventors conducted extensive research to achieve the above object. As a result, they found that a large amount of a primary culture of cancer cells could be stably obtained in vitro in a simple manner within a short time by subjecting cell masses derived from cancer tissues to suspension culture and then to adherent culture. The present invention has been accomplished based on these findings.

SUMMARY OF THE INVENTION

That is, the present invention provides the followings:
(1) A method for producing a primary culture of cancer cells, comprising following steps:

(a) fragmenting cancer tissues derived from a living body and removing impurities from the fragmented cancer tissues;
(b) subjecting the tissue masses obtained in step (a) to suspension culture; and
(c) subjecting the culture obtained in step (b) to adherent culture.
(2) The method according to (1), wherein the removing of the impurities may be performed by a method including sieving, and a lower limit size and an upper limit size of cell masses obtained by the sieving are 20 μm to 100 μm and 200 μm to 500 μm, respectively;
(3) The method according to (1) or (2), wherein the suspension culture may be performed for 24 to 48 hours;
(4) The method according to any of (1) to (3) comprising the following step:
(d) further subjecting the culture obtained in step (c) to subculture;
(5) A method of elucidating a molecular mechanism of cancer, performing a drug-susceptibility test, or screening a pharmaceutical, which comprises using the primary culture of cancer cells obtained by the method according to any of (1) to (4);
(6) A kit for elucidating a molecular mechanism of cancer, performing a drug-susceptibility test, or screening a pharmaceutical, which comprises the primary culture of cancer cells obtained by the method according to any of (1) to (4).

According to the present invention, a large amount of a primary culture of cancer cells can be stably obtained in vitro in a simple manner within a short time. The method for culturing primary cancer cells of the present invention can be applied to various kinds of cancer cells. The primary culture of cancer cells obtained by the present invention has characteristics similar to cancer tissues under a clinical condition, thus enabling to reproduce in vitro a condition of cancer tissues in a living body. As such, the use of the primary culture obtained by the present invention makes it possible to screen a pharmaceutical, perform a drug-susceptibility test, and study on elucidation of a molecular mechanism of cancer and the like accurately and efficiently. Further, according to the present invention, the primary culture having similar characteristics to cancer tissues of a patient can be obtained, thus such primary culture can be used for personalized therapy of the patient.

DESCRIPTION OF THE PREFERRED EMBODIMENTS

Figure 1:
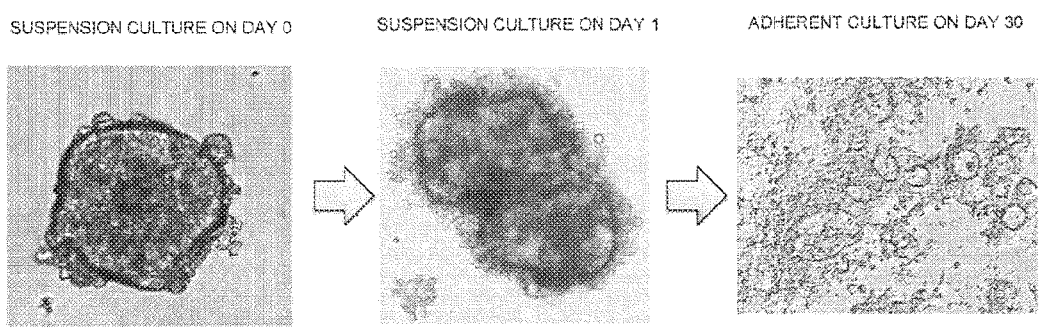
FIG. 1 shows microscopic images of colon cancer cell masses derived from a clinical sample on Day 0 (left) and Day 1 (middle) of suspension culture, and Day 30 (right) of adherent culture.

The present invention provides, in a first embodiment, a method for producing a primary culture of cancer cells, comprising the following steps: (a) fragmenting cancer tissues derived from a living body and removing impurities from the fragmented cancer tissues, (b) subjecting the tissue masses obtained in step (a) to suspension culture, and (c) subjecting the culture obtained in step (b) to adherent culture.

The step (a) of the above method is described below. The living body refers to a live animal, preferably a mammal, typically a human being having a cancer. Any means and method may be used to obtain cancer tissues from the living body. For example, the cancer tissues may be obtained by collection and extirpation during a surgical operation or obtained when performing a biopsy.

Any kind of cancers may be applied and examples of cancers include, but are not limited to, colon cancer, small intestine cancer, stomach cancer, esophagus cancer, anal cancer, pancreatic cancer, liver cancer, bile duct cancer, gastrointestinal endocrine tumor, gastrointestinal stromal tumor (GIST), breast cancer, lung cancer, mesothelioma, thymic carcinoma, renal cancer, urothelial cancer, testicular cancer, prostate cancer, uterine corpus cancer, cervical cancer, uterine sarcoma, ovarian malignant tumor, tongue cancer, gingival cancer, mouth floor cancer, pharyngeal cancer, laryngeal cancer, salivary gland cancer, thyroid cancer, osteosarcoma, Ewing's sarcoma, soft tissue sarcoma, myelodysplastic syndrome, skin cancer, neuroblastoma, malignant glioma (glioblastoma), malignant lymphoma, and multiple myeloma.

The cancer tissues obtained from the living body may be directly fragmented. or maintained in a medium for culturing an animal cell before fragmentation. Examples of the medium for culturing an animal cell include, but are not limited to, D-MEM, E-MEM, and RPMI-1640. Maintenance of the cancer tissues in the medium in this stage may be performed for an appropriate time, for example, several hours to 48 hours.

The cancer tissues may be washed before fragmentation. The washing may be performed in a physiological saline solution or a buffer solution such as a phosphate buffer solution, an acetic acid buffer solution, and a Tris buffer solution.

The fragmentation may be performed by any means and method, including the use of a knife, scissors, a cutter, and the like. For example, the cancer tissues may be shredded using scissors. Alternatively, a suspension of the cancer tissues may be repeatedly passed through a syringe having an injection needle of proper size for the fragmentation. The cancer tissues are preferably shredded until tissue masses can no longer be seen with the naked eye (diameter of about 1 mm or less).

The fragmented cancer tissues may be subjected to a treatment with enzyme(s) to remove connective tissues and the like. Examples of such an enzyme include, but are not limited to, collagenase, trypsin, papain, and dyspase. These enzymes may be used. singly or two or more of them may be used in combination.

Any means and method may be used to remove the impurities from the fragmented cancer tissues. The impurities may include contaminating microorganisms, tissue pieces other than the cancer tissues, and the like, but may also include other types of materials. The impurities may be removed by the washing and the enzyme treatment as described above, but preferably by a method including sieving.

Sieving may be performed by any means and method, but preferably by using a sterilized filter. A lower limit and upper limit of size of cell masses obtained by sieving can be set in accordance with kinds and histological types of cancers. The lower limit and upper limit are preferably set to about 20 μm to about 100 μm and about 200 μm to about 500 μm, respectively. The cell masses in such sizes can be obtained by selecting and sequentially using two filters each having an appropriate pore size. Filters of various pore sizes are commercially available. For example, the cell masses of a desired size can be recovered by suspending the cell masses, which pass through a filter having a pore size of 200 μm, but do not pass through a filter having a pore size of 20 μm and remain on the filter, in a physiological saline solution or a medium for culturing an animal cell and then performing, for example, centrifugal separation.

By making the size of the cell masses to be that mentioned above, contamination can be efficiently prevented and a ratio of viable cells in the cell masses also increases. This, in turn, increases an efficiency of the primary culture of cancer cells obtained through the next step, namely the suspension culture step and the third step, namely the adherent culture step. Further, selecting the cell masses according to the above size can reduce a ratio of fibroblasts and the like and make the primary culture obtained after the adherent culture more similar to actual clinical tissues.

In the step (b) of the above method, the cancer cell masses obtained as described above are subjected to the suspension culture. The suspension culture is a type of culture in which the cancer cell masses are cultured without adhering to a culture container. The suspension culture is known to a person skilled in the art. A culture container of which surface is treated for suppressing adhesion of cells or cell masses is commercially available and such a culture container may be used for the suspension culture. Further, a shape and size of the culture container can be selected according to conditions, such as kinds and a necessary quantity of cancer cells. A flask, bottle, dish, tube, and plate of various sizes are commercially available and they may be used. Other conditions related to the suspension culture, such as a composition of a medium, culture temperature, whether static, stirred, or shaken culturing is performed for the suspension culture, can be appropriately determined by a person skilled in the art according to kinds of cancer cells and other conditions.

In the present invention, cells capable of being transferred to the adherent culture can be selected more selectively by performing the suspension culture for an appropriate time. The suspension culture is preferably performed for about 24 hours to about 48 hours. When the cancer cell masses are subjected to the suspension culture for such a period of time and then subjected to the adherent culture, there are obtained a primary culture with morphology and characteristics similar to clinical tissues and having no mutations or few, if any, mutations in genes.

In the step (c) of the above method, the cancer cell masses grown by the suspension culture as described above are subjected to the adherent culture. In the adherent culture, the cancer cell masses are grown while attached to the culture container. The adherent culture is known to a person skilled in the art. A culture container of which surface is treated for facilitating adhesion of cells or cell masses is commercially available and such a culture container may be used for the adherent culture. For some kinds and histological types of cancers, the cancer cell masses may be seeded on a plate on which laminin-511, soluble E-cadherin, and the like are immobilized. Further, a shape and size of the culture container can be selected according to conditions, such as kinds and a necessary quantity of cancer cells. A flask, bottle, dish, tube, and plate of various sizes are commercially available and they may be used. A medium for the adherent culture can be also selected according to kinds of cancer cells and other conditions. Other conditions related to the adherent culture, such as kinds of media and culture temperature, can be also appropriately determined by a person skilled in the art.

By performing the adherent culture for an appropriate time, cells can be proliferated to produce a large amount of a primary culture of cancer cells. For example, the adherent culture may be performed in a manner such that cells are grown on a commercially available plate for adherent culture at 37° C. under 5% $CO_2$ while a culture medium being replaced every day or two until the cells are proliferated to occupy about 50% to about 80% of the plate, According to the method of the present invention, a large amount of a primary culture of cancer cells having similarity to clinical tissues can be obtained. That is, according to the present invention, a state of cancer tissues in a living body can be reproduced in vitro. Thus, the use of the primary culture obtained by the present invention makes it possible to elucidate a molecular mechanism of cancer, perform a drug-susceptibility test, screen a pharmaceutical, and the like accurately and efficiently. For those studies, the primary culture obtained by the present invention may be used in vitro or transplanted into an animal.

The step (b) of performing the suspension culture may be omitted in the aforementioned method for production of a primary culture of the present invention.

The primary culture obtained as above may be further subjected to subculture. Specifically, the primary cult obtained as above can be detached from the culture container and subjected to subculture by a routine procedure. By performing the subculture, more fresh primary culture can be obtained. The subculture is preferably performed by the number of times by which characteristics (morphological, genetic, physiological, etc.) of the primary culture are not altered.

The present invention provides, in a further embodiment, a method of elucidating a molecular mechanism of cancer, performing a drug-susceptibility test, or screening a pharmaceutical, using the primary culture obtained by the method of the present invention.

The present invention provides, in a further embodiment, a kit for elucidating a molecular mechanism of cancer, performing a drug-susceptibility test, or screening a pharmaceutical, including the primary culture obtained by the method of the present invention. The kit of the present invention may include a reagent and an instrument necessary for a test, an instruction manual of the kit, and the like in addition to the primary culture described above.

While the present invention has been described in connection with the method for culturing primary cells derived from cancer tissues, the method of the present invention can be applied to primary culture of any tissues without being limited to cancer tissues.

Hereinafter, the present invention will be described in greater detail by showing working examples, however the scope of the present invention is not limited by the working examples.

EXAMPLE 1

Example 1 Production of a Primary Culture Derived from Colon Cancer

Cancer tissues were excised during a surgery operation and washed with a physiological saline solution three times and then washed with 1% Antibiotic-Antimycotic(Priduct No. 15240062; ThermoFisher Scientific) in PBS three times. The washed cancer tissues were shredded using scissors. The cancer tissues were shredded until tissue masses could no longer be seen with the naked eye, to a size (diameter of 1 mm or less) capable of being sucked by a 10 mL pipette. The shredded tissue pieces were collected in a 50 mL Falcon tube and added with 10 mL of collagenase (1 mg/ml) (C6885; Sigma-Aldrich, St. Louis, Mo. USA). The reaction was performed at 37° C. for 15 min using a shaker (Bio Shaker, BR-13FP) at 200 rpm.

A solution containing the cell masses dispersed by the collagenase was subjected to separation with two kinds of filters. The cell masses, which passed through a filter having a pore size of 250 μm, but did not pass through a filter having a pore size of 50 μm and remained on the filter, were collected. A cell population remained on the second filter was suspended in a medium 1 and spun down by a centrifuge (KUBOTA, KN-70) at 1,500 rpm for 5 min. A composition of the medium 1 was as follows.

DMEM/F12
  Knockout serum replacement (Thermo Fisher Scientific, cat. 10828028) (20%)
    Sodium hydrogen carbonate (25 mM)
    L-ascorbic acid (0.1 mg/mL)
    Fibroblast growth factor 2 (4 to 100 ng/mL)
    Transforming growth factor-β (20 to 30 pM)
    β-mercaptoethanol (0.1 mM)
    4-aminobutanoic acid (1 mM)
    Lithium chloride (0.5 to 1 mM)
    Penicillin-streptomycin (1%)
    L-glutamine (1 to 4 mM)
Suspension culture After sucking supernatant, precipitate was resuspended in the medium 1. The culture liquid in which the cell population was suspended was seeded on a plate (CORNING, Ultra-Low Attachment Surface Polystyrene). A left panel of FIG. 1 shows a microscopic image of cell masses when starting the suspension culture. After performing the culture at 37° C. for 24 to 48 hours, the culture liquid containing the suspended cell population was recovered. A middle panel of FIG. 1 shows a microscopic image of cell masses on Day 1 (24 hours) of the suspension culture.

Adherent culture

The suspended cell population recovered as described. above was spun down, resuspended, and seeded on a plate (hESC-Matrigel coated plate). The culture was performed in the medium 1 described above using an incubator (temperature of 37° C., carbon dioxide concentration of 5%) while the culture medium (medium I described above) being replaced every day or two. The adherent culture was performed for 30 days to obtain a primary cell culture of the present invention. A right panel of FIG. 1 shows the primary cell culture obtained by performing the adherent culture for 30 days. A large amount of the primary culture of cancer cells similar to clinical tissues could be obtained. It is noted that continuing the suspension culture for a long period of time (60 days) without performing the adherent culture only resulted in increasing cell density of the suspended cell population and failed to produce the primary cell culture of the present invention.

Subculture

When the cells were proliferated to occupy about 50% to 80% of the plate, the cells were subjected to subculture by a following method. After sucking the culture liquid, the cells were washed with phosphate buffered saline twice. After adding Accutase (Innovative Cell Technologies, Inc. San Diego, Calif. USA) to the cells, the reaction was performed at a room temperature for 5 to 10 min. The reaction solution was diluted 5 times by DMEM/F12 to recover the cells. Centrifugation was performed using the centrifuge (KUBOTA, KN-70) at 1,500 rpm for 5 min. After sucking supernatant, precipitate was resuspended in the medium 1 and seeded on a plate (hESC-Matrigel coated plate). Cells obtained by performing the subculture had similar characteristics to the cells obtained by performing the above-mentioned adherent culture.

Primary cell culture were obtained in the same manner as the above using 26 samples obtained by surgical operations of colon cancer and 15 samples obtained by biopsies of colon cancer. These primary cell cultures had morphology similar to the cancer tissues under a clinical condition, and results of immunohistochemistry analysis were also similar between the primary cell cultures and the cancer tissues under a clinical condition. Results of immunocytochemistry analysis were also similar between the obtained primary cell and the cancer cell of the clinical tissues. Gene mutation analysis (KRAS, NRAS, BRAF) using PCR showed that the primary cells and the cancer cells of the clinical tissues exhibited the same gene expression patterns.

All of the primary cell cultures obtained from 26 surgical operations could proliferate and be passaged by the subculture. Of those, the primary cultures obtained from 15 surgical operations were transplanted into mice (see Working example 2) and all transplantation events turned out to be successful. The primary cell cultures obtained from the biopsies could proliferate in 90% of cases and be passaged by the subculture in 80% of cases.

EXAMPLE 2

Example 2 Transplantation of a Primary Culture into Mice

Figure 2:
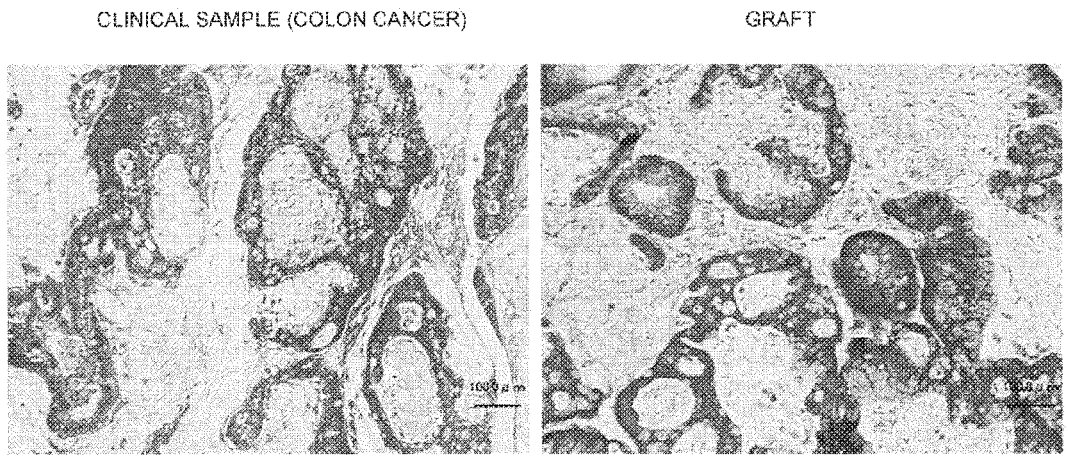
FIG. 2 shows microscopic images (HE staining) of tissue sections prepared from a clinical sample of colon cancer (left) and a graft (right) transplanted into a mouse (Day 42 after transplantation) using primary cultures derived from clinical samples of colon cancer, obtained by the present invention.

The primary cell culture ($1 \times 10^5$ cells) of colon cancer obtained in the same manner as in Example 1 was subcutaneously transplanted into NOD-SCID mice, The size of grafts increased in mice, demonstrating that the primary culture obtained by the present invention exhibited oncogenic potential. The grafts were analyzed on Day 42 after the transplantation. The grafts had morphology similar to the clinical samples (FIG. 2) and results of immunohistochemistry analysis were also similar between the grafts and the cancer tissues under a clinical condition. Results of immunocytochemistry analysis were also similar between the obtained primary cell and the cancer cell of the clinical tissues. Analysis by PCR showed that the primary cells and the cancer cells of the clinical tissues exhibited the same gene expression patterns.

EXAMPLE 3

Example 3 Production of a Primary Cell Culture from Various Cancer Tissues

Figure 3:
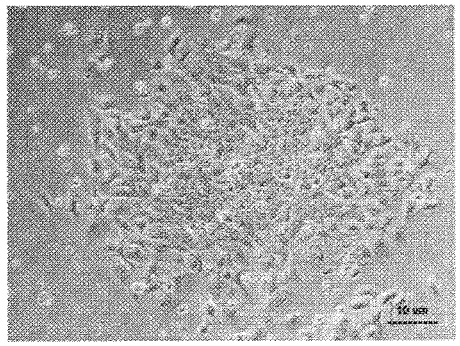
FIG. 3 shows microscopic images of primary cultures obtained by the method of the present invention, derived from clinical samples of stomach cancer (upper left), pancreatic cancer (upper right), and liver cancer (lower left).
Figure 3:
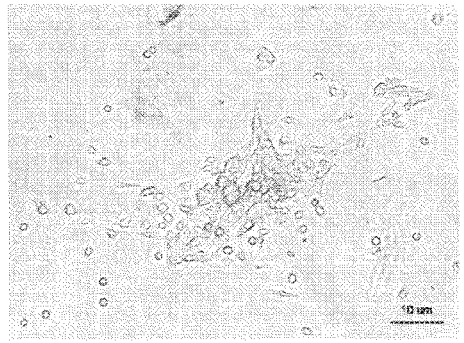
Figure 3:
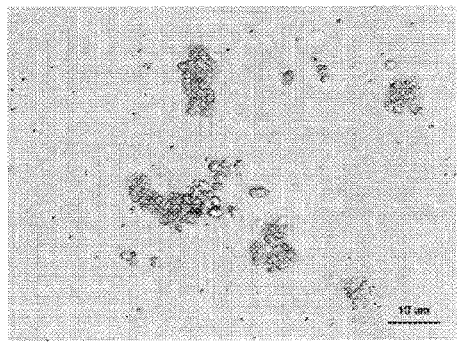
Figure 4:
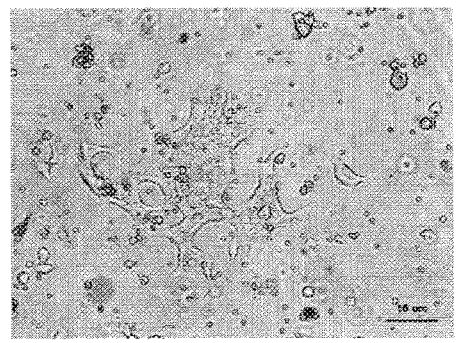
FIG. 4 shows microscopic images of primary cultures obtained by the method of the present invention, derived from clinical samples of lung cancer (upper left), renal cancer (upper right), and breast cancer (lower left).
Figure 4:
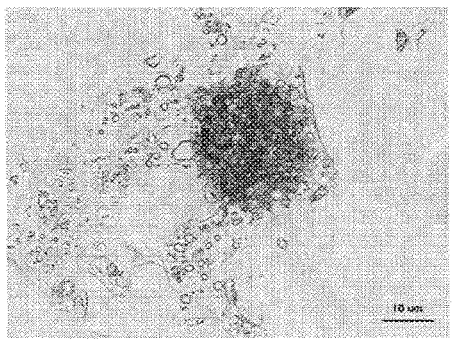
Figure 4:
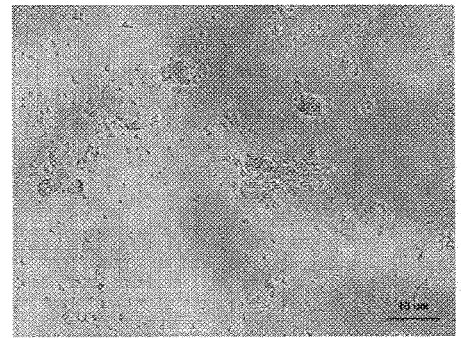

Primary cultures were obtained in the same manner as in Example 1 using samples collected by surgical operations and biopsies from tissues of stomach cancer, pancreatic cancer, liver cancer, lung cancer, renal cancer, and breast cancer. The primary cultures derived from the stomach cancer, the pancreatic cancer, and the liver cancer were shown in an upper left, upper right, and lower left panels, respectively, in FIG. 3. The primary cultures derived from the lung cancer, the renal cancer, and the breast cancer were shown in an upper left, upper right, and lower left panels, respectively, in FIG. 4. These results demonstrated that primary cells could be obtained from various kinds of cancer tissues using the method of the present invention.

The primary cultures of cancer cells obtained by the present invention have similar characteristics to cancer cells under a clinical condition, thus the present invention can be utilized in the fields of pharmaceutical development, cancer research, and the like.

What is claimed is:

1. A method for producing a primary culture of cancer cells, comprising:
    (a) fragmenting cancer tissues derived from a living body and removing impurities from the fragmented cancer tissues by sieving with a first filter having a pore size between 200 µm to 500 µm, and sieving with a second filter having a pore size between 20 µm to 100 µm;
    (b) collecting cell masses remaining on the second filter in (a);
    (c) subjecting the cell masses collected in (b) to suspension culture; and
    (d) subjecting the culture obtained in (c) to adherent culture,
    wherein the suspension culture is performed for 24 to 48 hours, and
    a lower limit size and an upper limit size of the cell masses obtained in (b) are 20 µm to 100 µm and 200 µm to 500 µm, respectively.

2. The method according to claim 1, further comprising: subjecting the culture obtained in (d) to subculture.

* * * * *